(12) United States Patent
Edmunds

(10) Patent No.: US 11,684,509 B2
(45) Date of Patent: Jun. 27, 2023

(54) COPPER-INCLUDING CONTRACEPTIVE SHIELD

(71) Applicant: Kathleen Edmunds, Knoxville, TN (US)

(72) Inventor: Kathleen Edmunds, Knoxville, TN (US)

( * ) Notice: Subject to any disclaimer, the term of this patent is extended or adjusted under 35 U.S.C. 154(b) by 199 days.

(21) Appl. No.: 17/300,378

(22) Filed: Jun. 7, 2021

(65) Prior Publication Data

US 2022/0031497 A1 Feb. 3, 2022

Related U.S. Application Data

(60) Provisional application No. 63/103,356, filed on Jul. 31, 2020.

(51) Int. Cl.
*A61F 6/08* (2006.01)
*A61F 6/14* (2006.01)
*A61K 9/00* (2006.01)
*A61K 33/34* (2006.01)

(52) U.S. Cl.
CPC .............. *A61F 6/08* (2013.01); *A61K 9/0036* (2013.01); *A61K 33/34* (2013.01)

(58) Field of Classification Search
CPC ... A61F 6/08; A61F 6/14; A61F 6/148; A61K 9/0036; A61K 33/34
See application file for complete search history.

(56) References Cited

U.S. PATENT DOCUMENTS

| | | | | |
|---|---|---|---|---|
| 3,683,906 A * | 8/1972 | Robinson | ................ | A61F 6/148 128/839 |
| 3,786,808 A * | 1/1974 | Lerner | .................... | A61F 6/148 128/839 |
| 3,834,378 A * | 9/1974 | Lerner | .................... | A61F 6/148 128/833 |
| 3,913,572 A * | 10/1975 | Wheeler | ................ | A61F 6/148 128/833 |
| 4,219,016 A * | 8/1980 | Drobish | .................... | A61F 6/06 128/832 |
| 7,040,323 B1 * | 5/2006 | Menchaca | ................ | A61F 6/14 128/833 |

* cited by examiner

*Primary Examiner* — Camtu T Nguyen
(74) *Attorney, Agent, or Firm* — Michael E. McKee

(57) ABSTRACT

A contraceptive device for intervaginal use includes a relatively thin, saucer-shaped impermeable body having two opposite side faces wherein one of the two side faces is concave in form and the other of the side faces is convex in form. In addition, the impermeable portion includes an amount of copper-including material which is disposed across the side faces of the impermeable portion so that the copper-including material is exposed at locations across the side faces.

14 Claims, 2 Drawing Sheets

COPPER-INCLUDING CONTRACEPTIVE SHIELD

BACKGROUND OF THE INVENTION

The benefit of Provisional Application Ser. No. 63/103,356, filed Jul. 31, 2020 and entitled COPPER-INCLUDING CONTRACEPTIVE SHIELD, is hereby claimed. The disclosure of this referenced provisional application is incorporated herein by reference.

This invention relates generally to contraceptive devices and relates, more particularly, to a contraceptive device for intravaginal use, such as a diaphragm.

The class of contraceptive devices with which this invention is concerned includes those possessing a body portion capable of being inserted within the vaginal canal of a user and which is capable of spanning the width of the vaginal canal. In addition, the body portion possesses outer edges which are substantially in sealing engagement with the walls of the vaginal canal.

Diaphragms used for contraceptive purposes commonly require that a spermicide gel be utilized with the diaphragm for effectiveness. However, such spermicide gels are messy to work with, and in the event that the diaphragm is frequently used, such spermicide gels must be applied to the diaphragm with a corresponding frequency.

It is an object of the present invention to provide a new and improved contraceptive device of the aforedescribed class.

Another object of the present invention is to provide such a contraceptive device to which a spermacide gel need not be added for effective use of the device.

Yet another object of the present invention is to provide such a contraceptive device which is uncomplicated in structure, yet effective in operation.

SUMMARY OF THE INVENTION

This invention resides in a contraceptive, device for intervaginal use.

The device includes a relatively thin, saucer-shaped impermeable body having two opposite side faces wherein one of the two side faces is concave in form and the other of the two side faces is convex in form. In addition, the impermeable portion includes an amount of copper-including material which is exposed at locations disposed across the side faces.

The impermeable body has an outer edge which can possess any of a number of shapes, such as oval or circular, and the composition of the impermeable body can provide the body with such a rigidity that the body cannot be collapsed or folded from side-to-side or can provide the body with a flexibility which permits the body to be collapsed from side-to-side to facilitate the insertion of the device into place. Accordingly, the impermable body may possess any of a number of shapes and can be flexible or inflexible in accordance with the broader aspects of the invention.

DETAILED DESCRIPTION OF AN ILLUSTRATIVE EMBODIMENT

Figure 1:
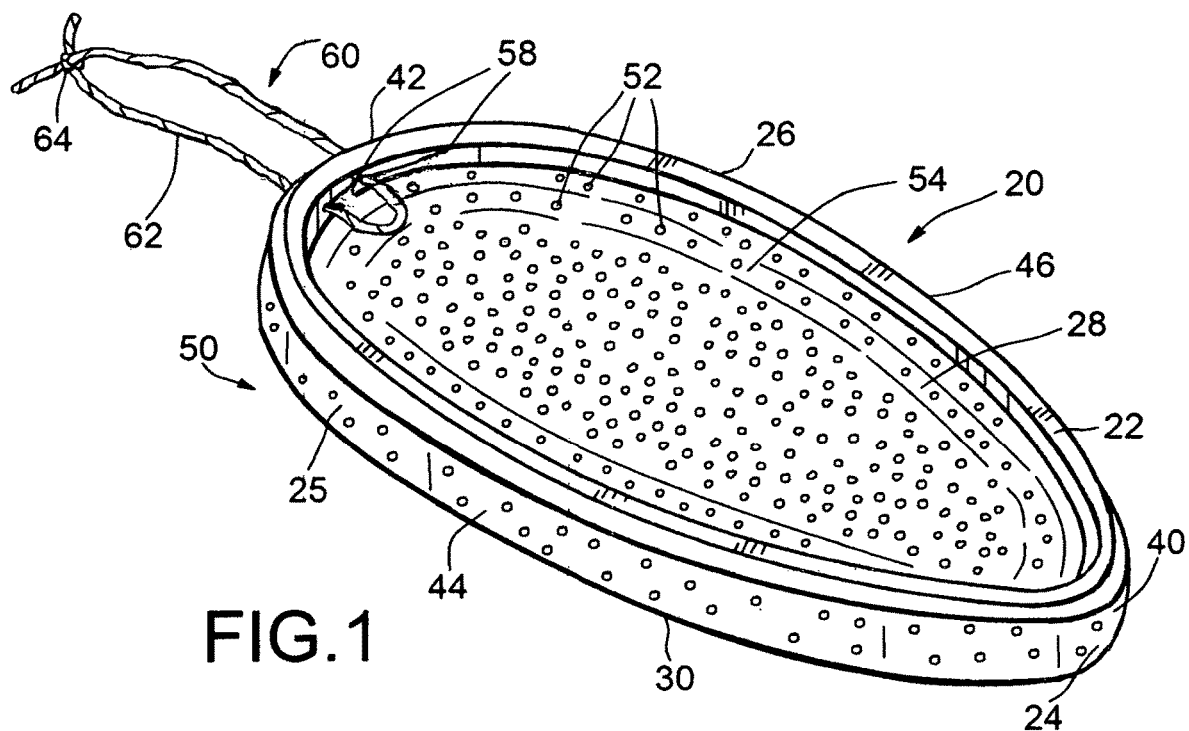
FIG. 1 is a perspective view of an embodiment of a contraceptive device within which features of the present invention are embodied.

Turning now to the drawings in greater detail and considering first FIG. 1, there is illustrated an embodiment, generally indicated 20, of a contraceptive device within which features of the present invention are embodied. Briefly, the embodiment 20 includes a liquid-impermeable portion 22 which is sized to be accepted by the vaginal canal of a user when inserted into place therein. As will be apparent herein, the impermeable portion 22 is adapted to provide a satisfactory seal between the outer edges of the impermeable portion and the walls of the vaginal canal to prevent passage of fluids past the impermeable portion 22.

Figure 2:
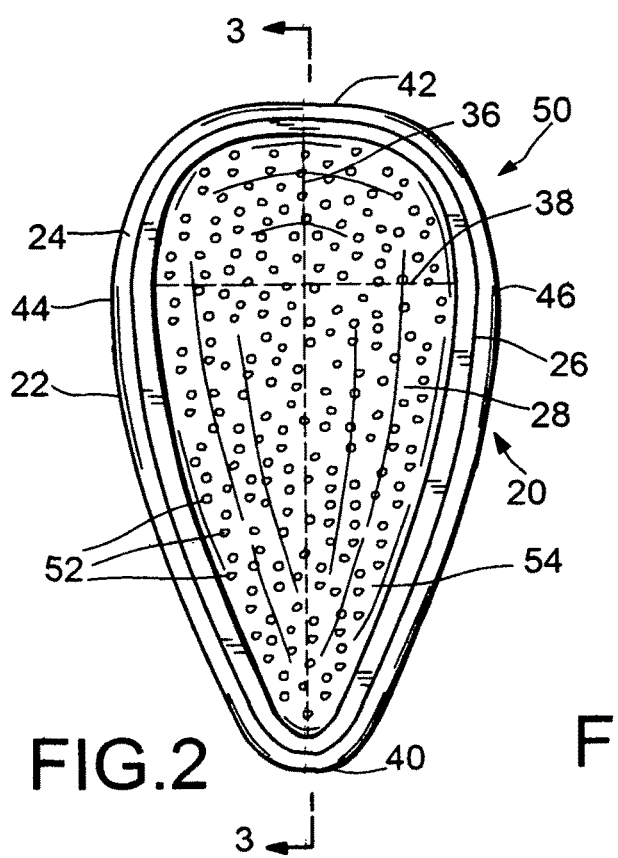
FIG. 2 is a plan view of the FIG. 1 device as seen generally from above in FIG. 1, but shown without the withdrawal cord attached therein.
Figure 3:
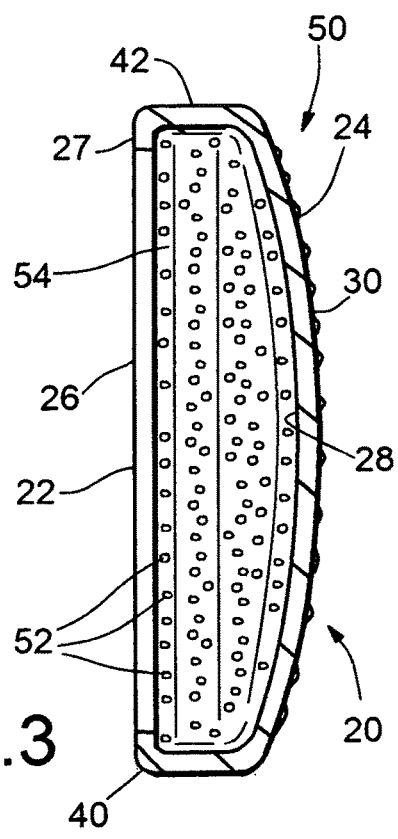
FIG. 3 is a longitudinal cross-sectional view of the FIG. 1 device taken along line 3-3 of FIG. 2.

With reference to FIGS. 1-3, the impermeable portion 22 is comprised of a body 24 of material which is saucer-shaped in form having a relatively shallow, concave side face 28 and an opposite convex side face 30. In addition, the impermeable portion 22 is relatively thin as measured between the side faces 28, 30, and the concave side face 28 is bounded by a relatively shallow sidewall 25 which extends in a direction which corresponds to the direction in which the concave side face 28 faces.

The impermeable portion 22 of the depicted contraceptive device 20 has an oval-shaped outer edge 26 (which can be provided with an inwardly-directed lip 27) to provide a better-fitting relationship between the outer edge 26 and the walls of the vaginal canal than can be had with circular-shaped devices of the prior art. It will be understood, however, that in accordance with the broader aspects of the present invention, the outer edge 26 can take an alternatively-shaped form, such as circular. Accordingly, the principles of the present invention can be variously applied.

The outer edge 26 of the impermeable portion 22 of the depicted device 20 (as best viewed in FIG. 2) is shaped to resemble an oval so that its maximum dimension (as measured along its major axis 36, indicated in phantom and extending through the center of the oval shape of the outer edge 26) is at least about 1.5 times the size of the minimum dimension (as measured along its minor axis 38, also indicated in phantom and extending through the center of the oval shape of the outer edge 26). Preferably, the oval-shaped outer edge 26 has a maximum dimension which is at least about 2.0 times the size of its minimum dimension. It has been found that the depicted assembly 20, with its oval-shaped impermeable portion 22, provides a better edge-to-vaginal canal sealing relationship than is capable of being formed with any impermeable portion of circular form and is advantageous in this respect.

While an oval, by definition, is symmetrical about at least one of its major or minor axes, the oval shape of the depicted impermeable portion 22 is symmetrical about each of its major and minor axes 36, 38. Therefore and more particularly, the shape of the outer edge 26 of the depicted impermeable portion 22 is elliptical. In a broad sense, therefore, the outer edge 26 of the impermeable portion 22 is oval, but in the embodiment of the assembly 20 depicted in FIGS. 1-3, the outer edge 26 of the impermeable portion 22 is elliptical in shape.

The device 20 of FIGS. 1-3 and, more specifically, the impermeable portion 22 of the device 20, is intended to be inserted endwise into place through the vaginal canal as the impermeable portion 22 is subsequently moved lengthwise (i.e. in a direction parallel to the major axis 36) through the canal. Accordingly and for present purposes, the leading end of the impermeable portion 22 (i.e. the end of the impermeable portion 22 which is inserted first through the vaginal canal 22) is indicted 40 in FIGS. 1-3, the opposite, or trailing, end of the impermeable portion 22 (i.e. the end of the impermeable portion 22 which follows the leading end 40 into place) is indicated 42 in FIGS. 1-3, and the opposite sides of the impermeable portion 22 which extend between the leading and trailing ends 40 and 42 are indicated 44 and 46 in FIGS. 1 and 4.

It is also a feature of the contraceptive device 20 that its impermeable portion 22 includes a copper-including component, generally indicated 50 in FIGS. 1-3 and which can be comprised of copper or a copper alloy, is exposed at several locations disposed along the outer surfaces of the side faces 28 and 30. The description herein of the copper-including component 50 being exposed at locations disposed across the side faces 28 and 30 of the body 24 means that portions of the copper-including component 50 defines, or provides, portions of the surfaces of the side faces 28 and 30. Stated another way, amounts of the copper-including component 50 are present along each of the concave side face 28 and the opposite convex side face 30 of the body 24. The copper-including component 50 is known to be a spermicide. Therefore and in practice—and when sperm comes into contact with a copper-including material, copper ions are released from the remainder of the copper-including material and detach the tails from the sperm from the remainder thereof. Without the tails, the sperm cannot penetrate an egg.

Heretofore, copper is known to be safe for use in the human body (i.e. it does not cause an adverse reaction when it comes into contact with skin or other tissue), is antimicrobial and has been known to kill bacteria, fungus and viruses. Consequently, applicant's incorporation of a copper-including material within her impermeable portion 22 for use as a spermicide is advantageous on a number of levels.

The incorporation of the copper-including material 50 within the impermeable portion 22 can take any of a number of forms, but in the depicted embodiment 30, the material 30 is in the form of relatively small spherical pellets 52 which are bound together in a mixture of pellets 52 and an amount of elastomeric material 54 and wherein surfaces of the pellets 52 are exposed along the surfaces (i.e. the concave side face 28 and the opposite convex side face 30) of the impermeable portion 22.

In the depicted embodiment 20, the elastomeric material 54 could provide the impermeable portion 22 with a degree of flexibility to enable compression (e.g. side-to-side) of the device 20 between the user's fingers and thereby facilitate insertion of the device 20 into place use in much the same manner that a flexible diaphragm is inserted into place. In the alternative, however, the impermeable portion 22 can be sized so that it does not need to be compressed (e.g. from side-to-side or between the fingers of a user) to facilitate the endwise insertion of the impermeable portion into place within the vaginal canal of a user. Consequently, the elastomeric material 54 can be comprised of a relatively hard plastic which prevents the body 24 from being compressed in size between the fingers of a user. However, latex might be avoided due to the allergic reaction that some individuals have to this material.

As mentioned above, the copper-including material 50, such as the depicted pellets 52, are exposed along the surfaces (i.e. the concave side face 28 and the opposite convex side face 30) of the impermeable portion 22. Because the purpose served by the copper-including material 50 is to negate the utility of any sperm which comes into contact with the copper-including material 50, the greater that the copper-including material 50 is exposed at the surfaces of the side faces 28 and 30 of the impermeable portion 22, the greater the sperm-negating capacity of the impermeable portion 22. The percentage of exposure of the copper-including material 50 to the total surface area of the impermeable portion 22 of the depicted device is at least about forty percent, but alternative percentages can be had.

It is an additional feature of the assembly 20 that it also includes means, generally indicated 60 in FIGS. 1, for facilitating the removal of the assembly 20 from its position of use within the vaginal canal. Within the depicted assembly 20, the facilitating means 60 includes a length of withdrawal cord or string 62 comprised, for example, of cotton, and which is looped through a pair of openings 58 formed in the impermeable portion 22 adjacent the trailing end 42 thereof and which is securely tied or otherwise secured, as with a knot 64 (FIG. 1), to secure the cord 62 to the impermeable portion 22 adjacent the end trailing end 42 thereof. Because the trailing end 42 of the impermeable portion 22 has been described above as being the end of the impermeable portion 22 which follows the leading end 40 of the impermeable portion 22 into the vaginal canal during installation, the trailing edge 42 is the first end of the impermeable portion 22 which exits the vaginal canal when withdrawn from the user. This being the case, the string 62 provides a visual indication to the user as to which end of the impermeable portion 22 corresponds with the trailing end 42 thereof.

Figure 4:
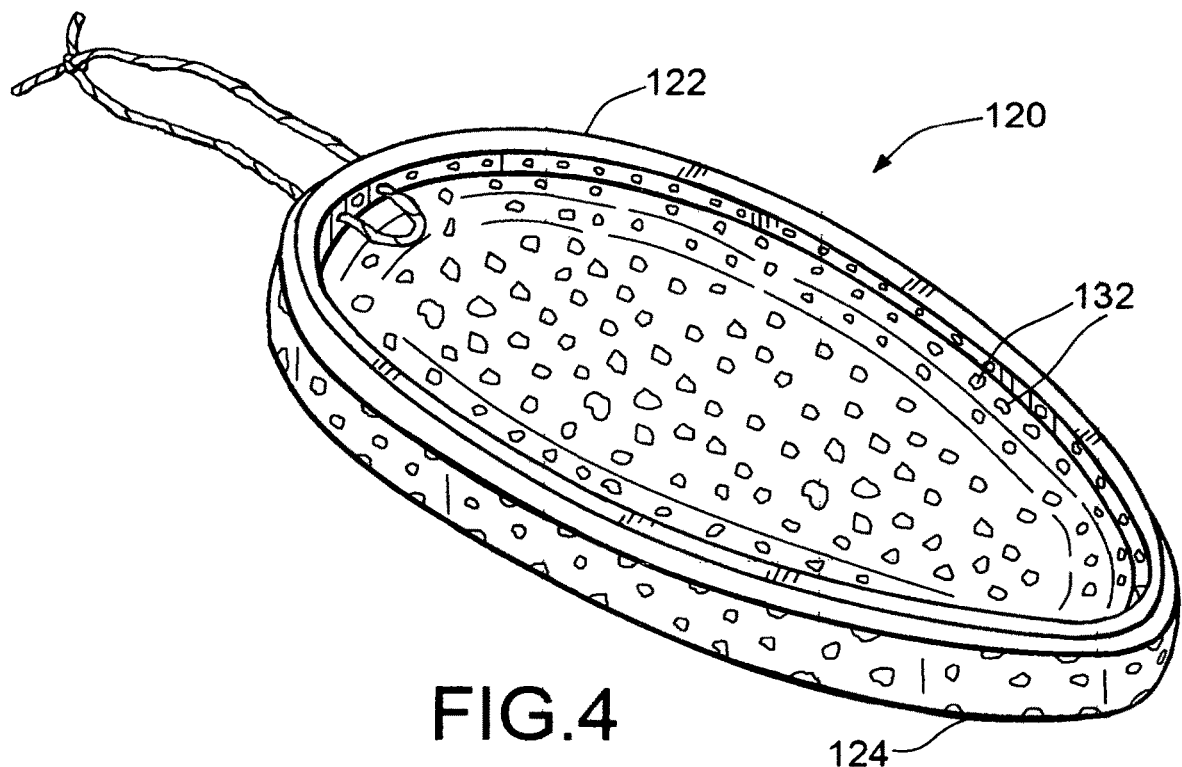
FIG. 4 is a perspective view of an alternative embodiment of a contraceptive device within which features of the present invention are embodied.

It will be understood that numerous modifications and substitutions can be had to the aforedescribed embodiment 20 of FIGS. 1-3 without departing from the spirit of the invention. For example, although the aforedescribed embodiment 20 has been shown and described as including spherically-shaped pellets 52 which comprise the copper-including material 50 of the impermeable portion 22, an embodiment which embodies the features of the present invention could include flakes of copper-including material. For example, there is illustrated in FIG. 4 an embodiment 120 having a body 122 of impermeable material comprised of flakes 132 of copper-including material which are embedded within (e.g. molded within) a body of elastomeric material 124.

Figure 5:
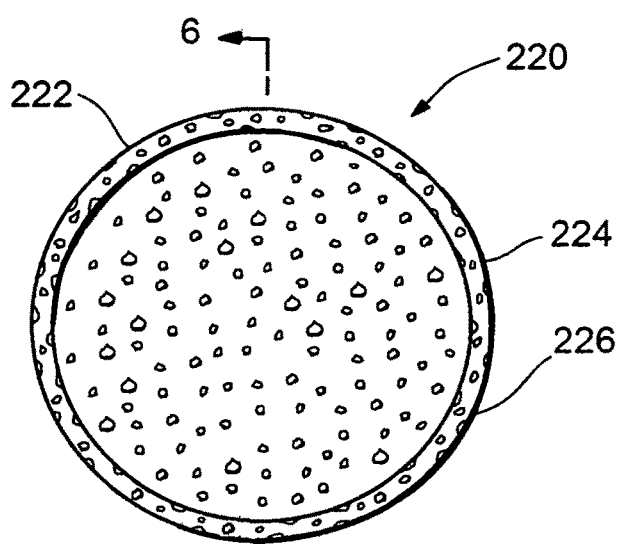
FIG. 5 is a plan view, similar to that of FIG. 2, of another embodiment of a contraceptive device within which features of the present invention are embodied.
Figure 6:
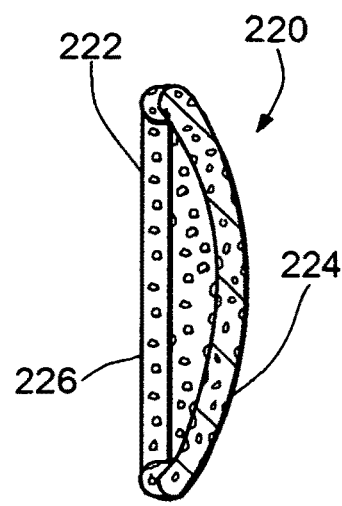
FIG. 6 is a longitudinal cross-sectional view of the FIG. 7 device taken along line 6-6 of FIG. 5.

Further still, although the impermeable portion 22 of the embodiment 20 of FIGS. 1-3 has been shown and described as including an outer edge 26 which possesses an oval shape, the impermeable portion of an alternative embodiment of the present invention can take an alternatively-shaped form, such as circular or substantially circular. For example, there is illustrated in FIGS. 5 and 6 an embodiment 220 having a body 222 of impermeable material 224 having an outer edge 226 which is circular in form.

Accordingly, the aforedescribed embodiment 20 of FIGS. 1-3 is intended for the purpose of illustration and not as limitation.

The invention claimed is:

1. A contraceptive device for intervaginal use comprising:
an impermeable portion having opposite outer surfaces and an outer edge adapted to be inserted into the user's vaginal canal so that when the device is inserted into the vaginal canal for use, the outer edge is positioned against and forms a seal with the walls of the vaginal canal to create a barrier to fluids passing therethrough; and
a copper-including material
(a) carried by the impermeable portion and
(b) exposed along the opposite outer surfaces thereof;
wherein the copper-including material is in a condition to release copper ions therefrom, causing a spermicidal effect; and
wherein one of the opposite outer surfaces is bounded by a sidewall which extends in a direction which corresponds to the direction in which the one of the opposite outer surfaces faces.

2. The device as defined in claim 1 wherein the percentage of exposure of the copper-including material to the total surface area of the outer surfaces of the impermeable portion is at least forty percent.

3. The device as defined in claim 1 wherein the impermeable portion possesses a body which is oval in shape, and the oval shape of the impermeable portion has a center and a largest dimension as measured across the center of the impermeable portion and a smallest dimension as measured across the center of the impermeable portion, and the largest dimension is at least 1.5 times the smallest dimension.

4. The device as defined in claim 1 wherein the copper-including material carried by the impermeable portion includes a plurality of spherical pellets having surfaces which are exposed along the outer surfaces of the impermeable portion.

5. The device as defined in claim 1 wherein one of the two opposite outer surfaces of the impermeable portion is concave in form and the other of the two opposite outer surfaces of the impermeable portion is convex in form.

6. The device as defined in claim 5 wherein the sidewall bounds the concave outer surface of the impermeable portion.

7. The device as defined in claim 1 wherein the impermeable portion possesses a rigidity which prevents the impermeable portion from being compressed into a folded condition.

8. The device as defined in claim 1 wherein the impermeable portion is oval in shape, and the oval shape of the impermeable portion is in the form of an ellipse.

9. A contraceptive device positionable within a vaginal canal and adjacent the cervix, said device comprising:
a thin fluid-impermeable body having two opposite side faces and an outer edge wherein one of the two opposite side faces is concave in form and the other of the two opposite side faces is convex in form, and the outer edge is adapted to be inserted into the user's vaginal canal so that when the contraceptive device is positioned therein for use, the outer edge is positioned against the walls of the vaginal canal to create a barrier to any fluids passing through the canal; and
wherein the impermeable body includes a mixture of elastomeric material and copper-including material; and
wherein the copper-including material is a) carried by the elastomeric material and is b) exposed at locations across each of the two opposite side faces of the impermeable body;
wherein the copper-including material is in a condition to release copper ions therefrom, causing a spermicidal effect; and
wherein one of the opposite side faces is bounded by a sidewall which extends in a direction corresponding to the direction faced by the one of the two opposite side faces.

10. The device as defined in claim 9 wherein the copper-including material of the impermeable body includes a plurality of spherical pellets which are exposed at locations disposed across each of the two opposed side faces of the impermeable material.

11. The device as defined in claim 9 wherein the outer edge of the impermeable body is oval in shape, and the oval shape of the impermeable body has a largest dimension as measured across the center of the impermeable body and a smallest dimension as measured across the center of the impermeable body, and the largest dimension is at least 1.5 times the smallest dimension.

12. The device as defined in claim 11 wherein the oval shape of the outer edge of the impermeable body is elliptical.

13. The device as defined in claim 9 wherein the thin fluid-impermeable body includes a leading end which first enters the vaginal canal when positioned within a user and an opposite trailing end, and the device further includes a cord which is securely attached to the impermeable body adjacent the trailing end thereof for facilitating the removal of the device following use.

14. A contraceptive device for intervaginal use comprising:
a body comprised of an impermeable material having opposite exterior surfaces and an outer edge adapted to be inserted into the user's vaginal canal so that when the contraceptive device is inserted into the vaginal canal for use, the outer edge is positioned against and forms a seal with the walls of the vaginal canal to thereby create a barrier to fluids passing through the vaginal canal; and
a copper-including material carried by the impermeable material and b) exposed along the opposite exterior surfaces thereof;
wherein the copper-including material is in a condition to release copper ions therefrom, causing a spermicidal effect; and
wherein at least one of the opposite exterior surfaces is bounded by a sidewall which extends in a direction which corresponds to the direction in which the at least one of the opposite exterior surface faces.

\* \* \* \* \*